United States Patent [19]

Kazuhiro et al.

[11] Patent Number: 4,574,783

[45] Date of Patent: Mar. 11, 1986

[54] ENDOSCOPE

[75] Inventors: Sakamoto Kazuhiro, Kita-saitama; Oshiro Susumu, Iwatsuki; Morioka Masaharu, Ageo, all of Japan

[73] Assignee: Fuji Photo Optical Co., Ltd., Saitama, Japan

[21] Appl. No.: 671,186

[22] Filed: Nov. 14, 1984

[30] Foreign Application Priority Data

Nov. 14, 1983 [JP] Japan ................................ 58-213584

[51] Int. Cl.4 .............................................. A61B 1/06
[52] U.S. Cl. ......................................................... 128/4
[58] Field of Search ........................................ 128/4, 6

[56] References Cited

U.S. PATENT DOCUMENTS 4,367,730 1/1983 Tanaka ...................................... 128/6

Primary Examiner—William H. Grieb
Attorney, Agent, or Firm—Koda and Androlia

[57] ABSTRACT

The present invention is applied to endoscopes for the medical purpose to observe cavities in a body such as a stomach, a duodenum, a bronchus or the like and endoscopes for the industrial purpose to observe the interiors of a machine or component such as an engine. The endoscope according to the invention comprises: an insertable portion to be inserted into a portion to be observed in the cavity of body or the machine or component; a manual control portion connected to the proximal end of the insertable portion and having an ocular portion; and a connecting portion connected at one end thereof to the manual control portion and connected at the other end thereof to an external apparatus having a power source through a connector thereof. In the endoscope of this type, the connector can be removed from the external apparatus and water-tightly connected to the ocular portion. As a result, even if the endoscope is immersed in an antiseptic solution or the like in this state, the endoscope can be immediately used without the ocular portion and the connector being moistened.

5 Claims, 7 Drawing Figures

FIG.1
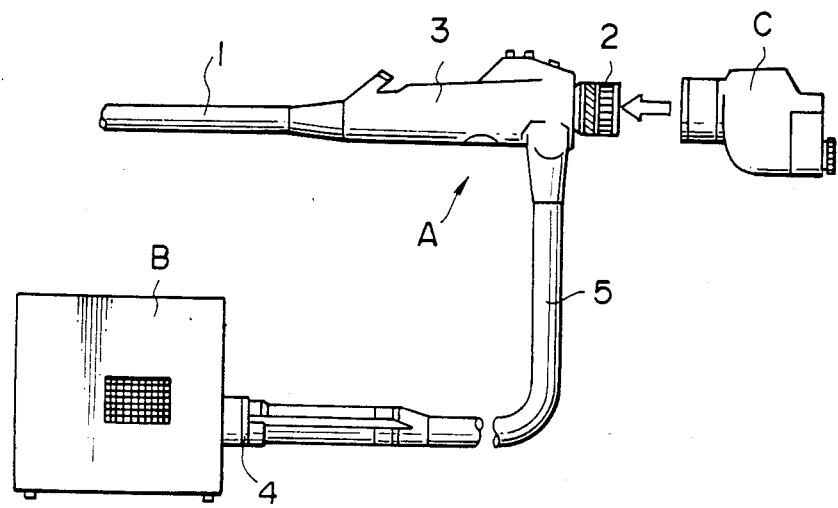
FIG.4
(A) 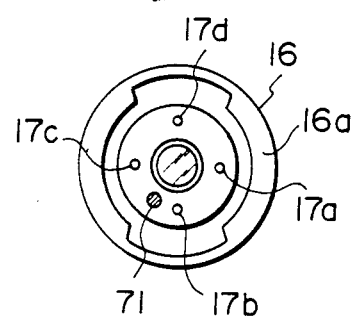
(B) 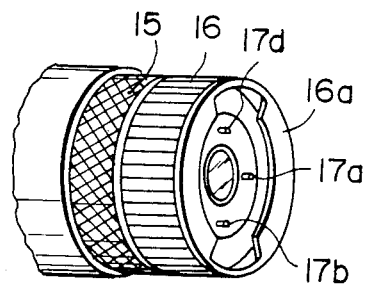

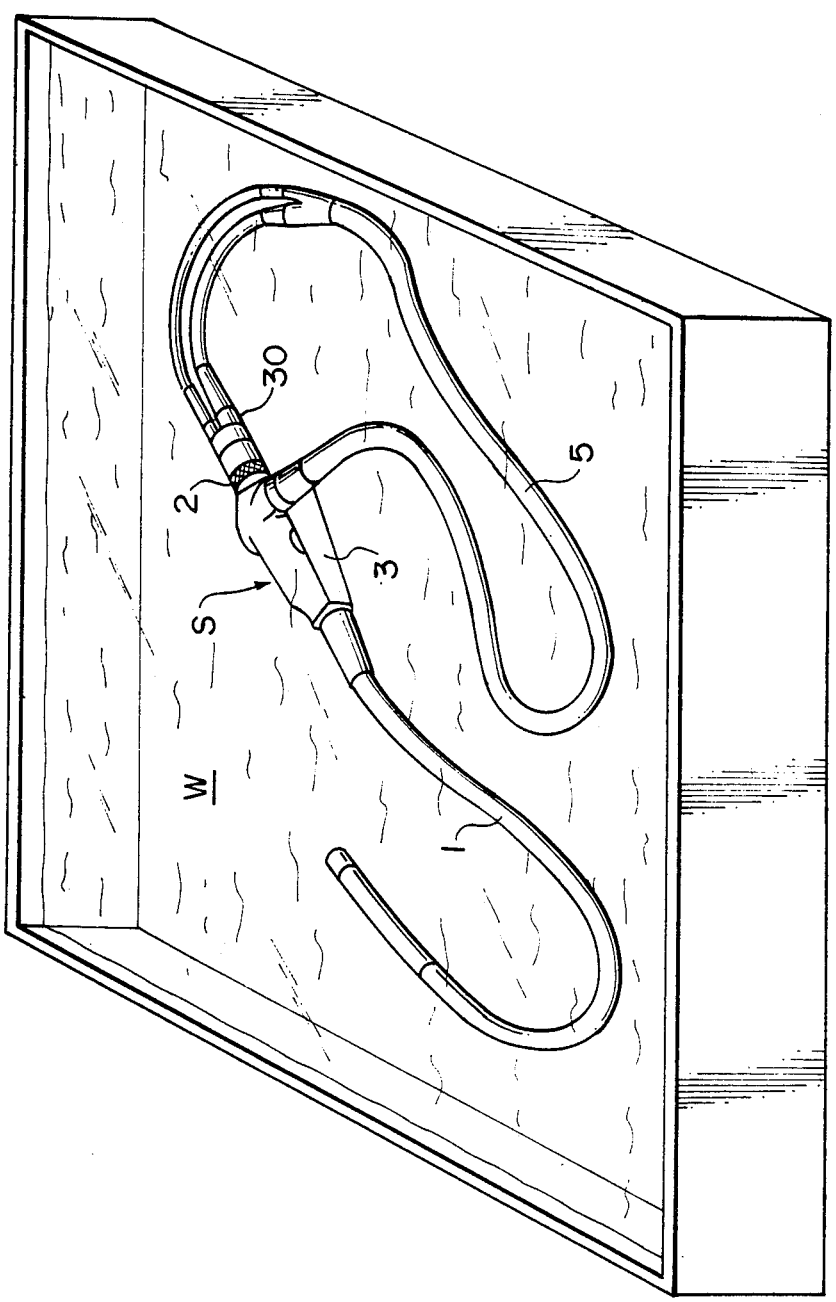

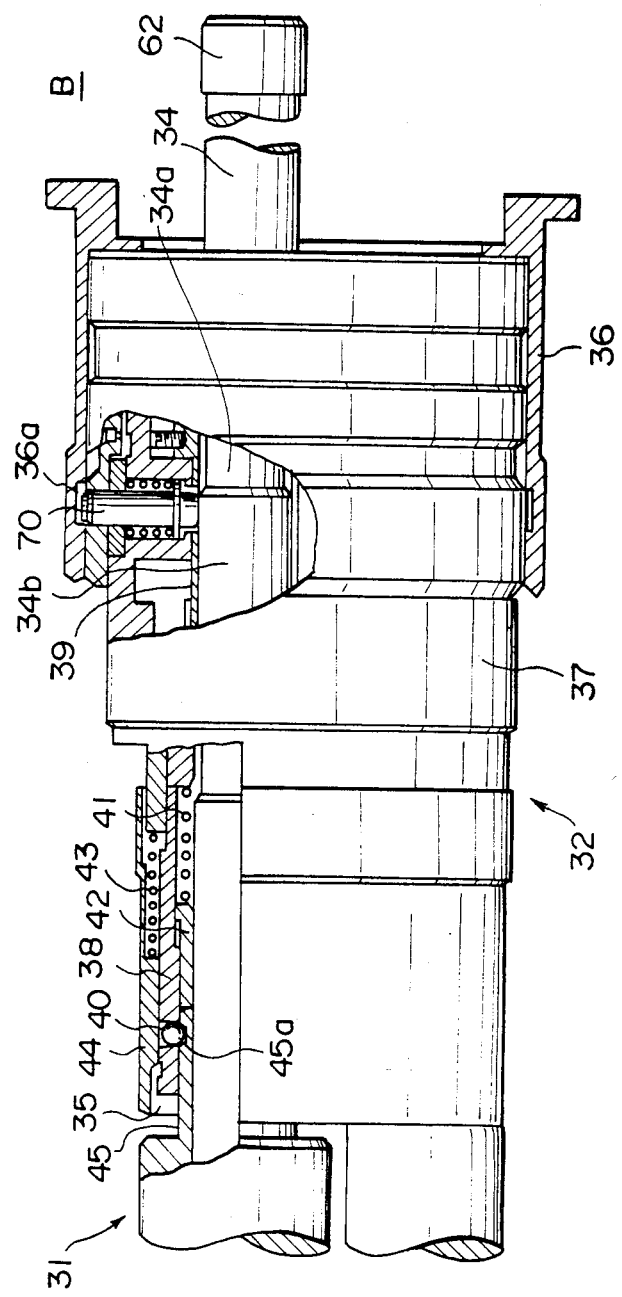

ENDOSCOPE

BACKGROUND OF THE INVENTION

1. Field of the Invention

This invention relates to endoscopes, and more particularly to an endoscope which can be wholly immersed in a washing liquid or an antiseptic solution.

2. Description of the Prior Art

Endoscopes are divided into two types including endoscopes for the medical purpose to observe cavities in a body such as a stomach, a duodenum, a bronchus and the like and endoscopes for the industrial purpose to observe the interiors of a machine or component such as an engine. Each of these endoscopes is generally constructed as shown in FIG. 1. More specifically, referring to FIG. 1, reference character A designates an endoscope comprising: an insertable portion 1 to be inserted into a portion to be observed in the cavity of body, or the machine or component; a manual control portion 3 connected to the proximal end of the insertable portion 1 and having an ocular portion 2 and the like; and a connecting portion 5 connected at the proximal end thereof to the manual control portion 3 and detachably connected to an external apparatus B through a connector 4 provided at the forward end thereof. The interiors of the cavities of body and the machine or component can be observed through the ocular portion 2, and further, a camera C for recording observed images can be installed onto the ocular portion 2.

The endoscope A generally constructed as described above transmits an irradiating light from a lamp of xenon, halogen or the like provided in the external apparatus B to the forward end of the insertable portion 1 to irradiate the interior of an object to be observed through optical fibers for transmitting the irradiating light, which are provided in the connecting portion 5, manual control portion 3, insertable portion 1, so that, through an observation optical system including an objective optical system, optical fibers for transmitting images, an ocular optical system as arranged in the above-described order from the forward end of the insertable portion 1, the object is observed through the ocular portion 2 or photographed by means of the camera C coupled to the ocular portion 2.

In order to take a photograph with the camera C, in the endoscope A between the ocular portion 2 coupled thereonto with the camera C and the connector 4 as being a connection to the external apparatus B, there are incorporated a power cable for the power supply to an electric circuit of the camera C from the external apparatus B and a signal cable for the signal delivery to an exposure control portion of the external apparatus from the camera C. In consequence, a plurality of electrode terminals are exposedly provided on the ocular portion 2 and the connector 4, respectively.

The above-described arrangement is the general arrangement belonging to the endoscopes well known so far. Recently, necessity has been voiced for the capabilities of being washed and disinfected of the endoscopes with the above-described arrangement, particularly, ones for the medical purpose from the viewpoint of sanitation. In general, it is said that liquid washing and liquid disinfection are most simple and perfect as the washing and disinfection applied to the endoscopes. In consequence, the endoscopes capable of being wholly immersed in such solutions as described above should be the endoscopes having the most desirable arrangement. However, in the conventional endoscope, although the insertable portion is perfectly waterproof, the electrode terminals on the ocular portion and the connector are exposed. Therefore, once the ocular portion or the connector portion is moistened, it becomes difficult to drain and dry the moistened portion, thus presenting such a disadvantage that the endoscope cannot be used immediately after the washing and disinfecting the endoscope.

In consequence, in the endoscopes, which have been proposed and put to the practical use, in order to obviate the aforesaid disadvantages, there have been taken such measures that a cover member is provided for water-tightly covering some portions of the electrode terminals, i.e. portions not desirable to be immersed in a liquid during the immersion of the endoscope in the liquid, or shapes of such portions as described above are changed and an adapter is utilized when such portions are connected to the external apparatus or the like, thereby resulting in inconvenience in handling.

SUMMARY OF THE INVENTION

The present invention has been developed to obviate the above-described disadvantages of the prior art and has as its object the provision of an endoscope, wherein an ocular portion and a connector, which have electrode terminals, are not moistened.

To this end, the present invention contemplates that:
the endoscope includes: an insertable portion to be inserted into a portion to be observed; a manual control portion secured thereto with the proximal end of the insertable portion; an ocular portion provided on the manual control portion; and a connecting portion having a connector secured at one end thereof to the manual control portion and detachably connected at the other end thereof to an external apparatus; and
the connector is water-tightly connected to the ocular portion.

BRIEF DESCRIPTION OF THE DRAWINGS

FIG. 1 is a schematic diagram showing the conventional endoscope;

FIGS. 2 to 7 show one embodiment of the endoscope according to the present invention, in which, FIG. 2 being a perspective view showing a state of the endoscope immersed in a liquid, FIG. 3 a sectional view of the essential portions showing a state where the connector portion of the connecting portion is connected to the ocular portion, FIGS. 4A and 4B explanatory views of the essential portions illustrating the ocular portion, FIG. 5 a sectional view of the essential portions showing a state where the connector portion of the connecting portion is connected to the external apparatus, FIG. 6 a perspective view of the essential portions showing the connector portion of the connecting portion, and FIG. 7 a sectional view taken along the line VII—VII in FIG. 3.

DETAILED DESCRIPTION OF THE INVENTION

Figure 3:
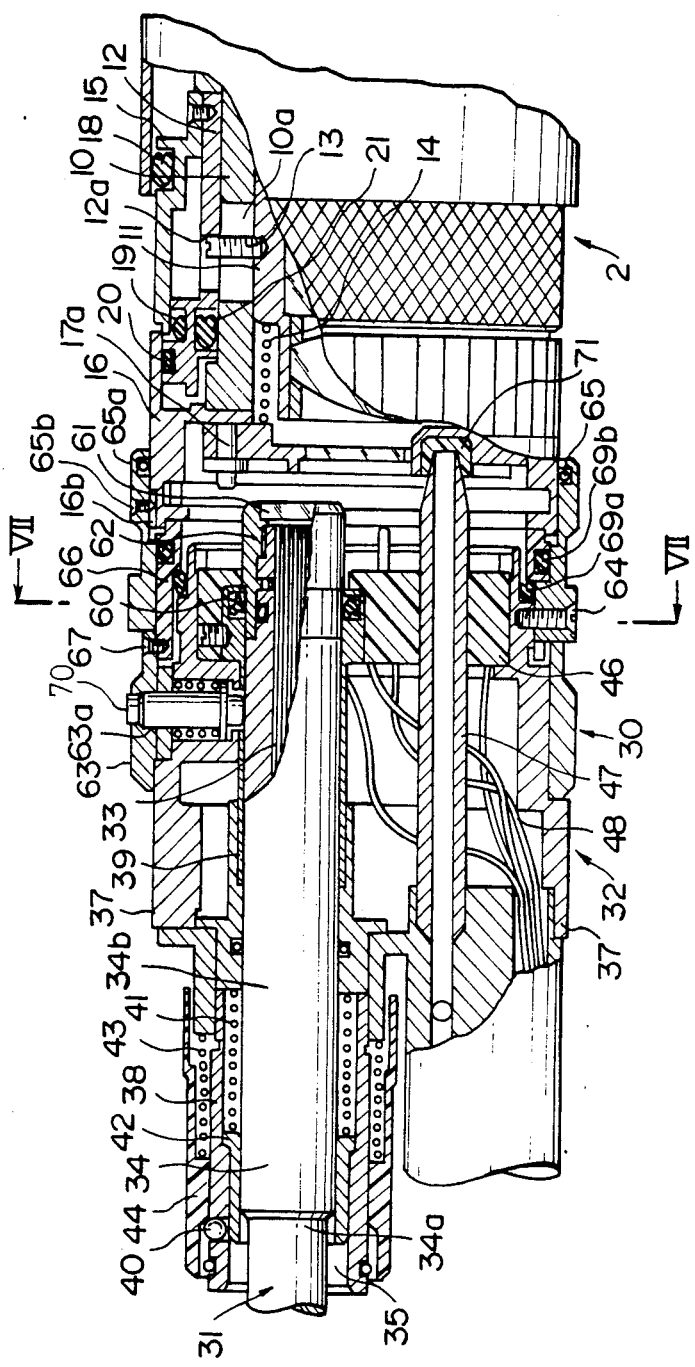

FIG. 2 shows a state where the endoscope S constructed according to the present invention is wholly immersed in a washing liquid and antiseptic solution tank W. The endoscope S is identical with the endoscope A in constructions of the insertable portion 1, ocular portion 2, manual control portion 3 and so forth, except the connector portion 4. These portions in FIG. 2 are designated by the same reference characters as used in FIG. 1. As apparent from FIG. 2, the forward end of the connecting portion 5 is coupled to the ocular portion 2, whereby the connecting portion 5 and the ocular portion 2, both of which require hermetical sealing, are hermetically sealed. As shown in FIG. 3, the ocular portion 2 includes: a stationary tube 10 solidly secured to the manual control portion 3; an eye piece holding tube 11 provided in the stationary tube 10 in a manner to be linearly movable in the direction of the optical axis; a visibility adjusting cam tube 12 coupled onto the outer periphery of the stationary tube 10; a cam follower pin 13 planted in the eye piece holding tube 11, which is engaged with a cam 12a of the cam tube 12 through a straight-lined keyway 10a along the optical axis of the stationary tube 10; a spring 14 for urging the cam follower pin 13 against the cam 12a of the visibility adjusting cam tube 12; and a visibility adjusting control ring 15 solidly secured to the outer periphery of the visibility adjusting cam tube 12. Rotation of the visibility adjusting control ring 15 causes the visibility adjusting cam tube 12 to rotate integrally therewith, whereby the cam 12a of the cam tube 12 linearly moves the eye piece holding tube 11 in the direction of the optical axis through the cam follower pin 13, so that the visibility can be adjusted. Furthermore, in addition to the above arrangement, this ocular portion 2 is provided with a stationary ring 16 solidly secured to the stationary tube 10. Provided on the end face of this stationary ring 16 on the ocular side are bayonet mounts 16a for installing an adapter device such as the camera C and the like in bayonet joint as shown in FIGS. 4A and 4B. Additionally, provided on the end face of the ocular portion 2 are electrode terminals 17a to 17d of the aforesaid power cable and the signal cable. Referring to FIG. 3, designated at 18 to 21 are waterproof packings for preventing water from intruding into the ocular portion 2.

Description will hereunder be given of the arrangement of a connector portion 30 on the side of the connecting portion 5, which is connected to the ocular portion 2. The connector portion 30 includes a first connector portion 31 and a second connector portion 32, which are bifurcated at the forward end of the connecting portion 5. The first connector portion 31 assumes a shape of rod-shaped sheath 34 envelopingly holding the incident end portion of optical fibers 33 for transmitting an irradiating light, extending through an insertion hole 35 formed in the second connector portion 32, and the incident end face of the optical fibers 33 for transmitting an irradiating light is positioned in a focusing surface of the power source in the external apparatus B. The second connector portion 32 is coupled to a socket 36 of the external apparatus B during the use of the endoscope as shown in FIG. 5, and has a support tube 37 positioned at the forward end of the connecting portion 5. Solidly secured to this support tube 37 are a stationary tube 38 formed therein with an insertion hole 35 for receiving the first connector portion 31 and a guide tube 39. The stationary tube 38 is provided therein with a dislodge locking mechanism for locking the first connector portion 31 inserted by a predetermined value. This dislodge locking mechanism includes: a stopper ball 40 loosely coupled in a through-hole formed in a side wall of the stationary tube 38 and having a diameter larger than the wall thickness of the stationary tube 38; a sliding tube 42 slidably provided in the stationary tube 38 in a manner to remove this stopper ball outwardly, biased by a spring 41 toward an insertion opening and regulated in its movement by a shoulder of the stationary tube 38; and a dislodge locking release control tube 44 coupled onto the outer periphery of the stationary tube 38, biased by a spring 43 toward the insertion opening and regulated in its movement by the stopper ball 40.

According to the above arrangement, under the state as shown in FIG. 3, the first connector portion 31 is inserted into the insertion hole 35 of the second connector portion 32 by a predetermined value as shown in FIG. 5, whereby an engageable tube 45 provided on the first connector portion 31 causes the sliding tube 42 to be pushed in against the biasing force of the spring 41, the stopper ball 40 is engaged with an engageable groove 45a of the engageable tube 45 and the dislodge locking release control tube 44 moves to a position shown in FIG. 5 to prevent the stopper ball from moving, so that the first connector portion 31 can be locked against dislodging. Additionally, the release of dislodge locking is carried out by the return of the dislodge locking release control tube 44 to the state shown in FIG. 3.

Further, the support tube 37 of the second connector portion 32 is provided therein with a lock pin 70 for locking the second connector portion 32 against dislodging from the socket 36 when the first connector portion 31 is inserted into the insertion hole 35 of the second connector portion 32 by the predetermined value after the second connector portion 32 is inserted into the socket 36 of the external apparatus B. This lock pin 70 is provided in a manner to be movable in the radial direction of the support tube 37, the inner end thereof extends through the guide tube 39 and biased to project into the insertion hole 35, into which the first connector portion 31 is coupled, and the outer end thereof is engageable with an inner peripheral groove 36a of the socket 36 as shown in FIG. 5. According to the above arrangement, when the first connector portion 31 is inserted into the second connector portion 32 before the coupling to the socket 36 of the external apparatus B is made, a small diameter portion 34a of the rod-shaped sheath 34 of the first connector portion 31 is opposed to the position of the lock pin 70 projecting inwardly, and, when the coupling is made as shown in FIG. 5, the lock pin 70 is projected outwardly into a large diameter portion 34b of the rod-shaped sheath 34, so that the outer end of the lock pin 70 can be engaged with the inner peripheral groove 36a.

Furthermore, a retainer disk 46 formed of an electric insulating material is solidly secured to an end face of the support tube 37 of the second connector portion 32. This retainer disk is formed therein with a through-hole, through which the rod-shaped sheath 34 of the first connector portion 31 extends, and solidly secured thereto with a connecting piece 47 for a gas feed pipe and pin-shaped electrode terminals 49 to 54 (Refer to FIGS. 6 and 7), which are connected to the power source cable, signal cable 48 and the like.

The constructions of the ocular portion 2 and the connector portion 30 as described above are identical with the constructions disclosed in Japanese Utility Model Application No. 128690/80 (Utility Model Kokai (Laid-Open) No. 51502/82) and Utility Model Application No. 191363/80 (Utility Model Kokai (Laid-Open) No. 113101/82) which have been filed by the applicant of the present patent, and hence, detailed description thereof will not be repeated.

In this embodiment of the present invention, in addition to the above arrangement, a waterproof packing 60 for holding the water-tightness between the guide tube 39 and the rod-shaped sheath 34 is provided in the guide tube 39 formed therein with the insertion hole 35 for receiving the first connector portion 31, and a waterproof cap member 62 holding a heat resistant glass 61 is detachably coupled to the forward end of the first connector portion 31. This cap member 62 includes a portion having an outer diameter larger than an inner diameter of the guide tube 39, so that the first connector portion 31 cannot be drawn out from the state shown in FIG. 3.

Figure 7:
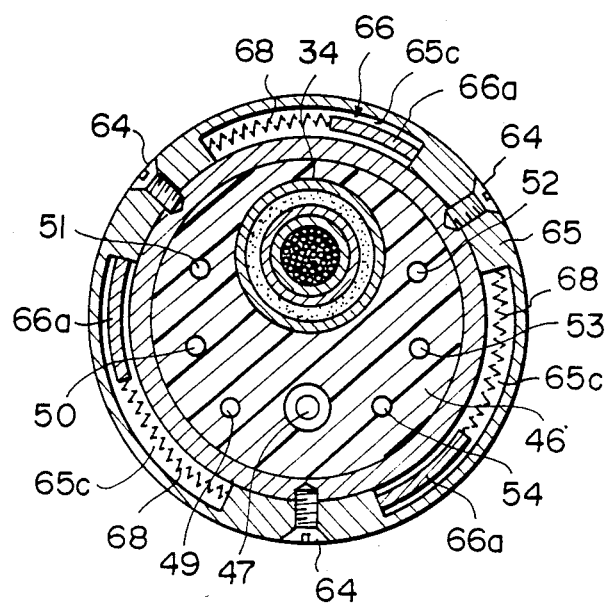

Further, as shown in FIG. 3, the second connector portion 32 is rotatably provided on the outer periphery of the support tube 37 thereof with a control ring 63, and a connection cover tube 65 is fixed to the support tube 37 through a locking screw 64. The control ring 63 is formed therein with a hole 63a elongate in the circumferential direction at a position opposed to the lock pin 70, thereby permitting the projection of the lock pin 70 and the rotation of the control ring 63 through a required value. Furthermore, the connection cover tube 65 is coupled onto the outer periphery of the stationary ring 16 of the ocular portion 2, and a waterproof packing 65a for holding the water-tightness with the outer peripheral surface of the stationary ring 16 of the ocular portion 2 is provided on the inner peripheral surface of the connection cover tube 65 around the opening end thereof. Further, provided on the inner surface of the connection cover tube 65 is a guide pin 65b engageable with a guide groove 16b formed on the outer peripheral surface of the stationary ring 16 along the optical axis. As shown in FIG. 7, three cutaway portions 65c, 65c and 65c are formed on the inner surface of the connection cover tube 65, in each of which portions of a connecting tube 66 fixed to the control ring 63 through a locking screw 67 are disposed, respectively. Three raised portions 66a, 66a and 66a are provided on one end of the connecting tube 66. The raised portions 66a, 66a and 66a of the connecting tube 66 are rotatably biased by springs 68, 68 and 68 which are provided in the cutaway portions 65c, 65c and 65c of the connection cover tube 65 in the clockwise direction in FIG. 7. Provided on the other end face of this connecting tube 66 are two engageable pawls 66c (only one pawl is shown in the drawing) to be connected in bayonet joint to bayonet mounts 16a shown in FIGS. 4A and 4B. These engageable pawls 66c are provided in such a positional relationship that, when the guide groove 16b of the stationary ring 16 is engaged with the guide pin 65b of the connection cover tube 65, inclined surfaces at the forward ends of the engageable pawls 66c are brought into abutting contact with the side edges of openings of the bayonet mounts 16a for receiving the engageable pawls 66c. Referring to FIG. 3, designated at 69a and 69b are waterproof packings for holding the water-tightness between the support tube 37, the connecting tube 66 and the connection cover tube 65 and between the connecting tube 66 and the connection cover tube 65, respectively. Further, denoted at 71 is a receiving seat opposed to the forward end of the mouth piece 47 for the gas feed pipe provided on the end face of the ocular portion 2. This receiving seat 71 is formed of an elastic material such as rubber, for blocking an opening at the forward end of the mouth piece 47 and preventing the counterflow through the gas feed pipe.

Needless to say, the endoscope S with the above arrangement, when in use, the connector portion 30 can be connected to the external apparatus B shown in FIG. 1, and the camera or the like can be coupled to the ocular portion 2, so as to be handled in the same manner as before. Moreover, with the following operation, the endoscope S as a whole can be immersed in the liquid such as washing water or an antiseptic solution as shown in FIG. 2 without the end faces of the ocular portion 2 and the connector portion 30 are moistened.

Figure 6:
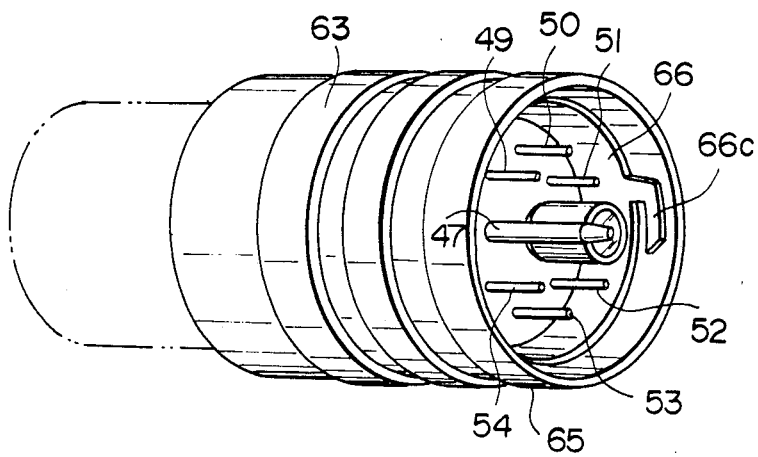

More specifically, in this endoscope S, after the use, the first connector portion 31 is drawn out of the second connector portion 32 until the cap member 62 at the forward end of the first connector portion 31 abuts against the forward end of the guide tube 39, and thereafter, the connector portion 30 is connected to the ocular portion 2 in an end-to-end relation. During this connecting operation, the guide groove 16b of the stationary ring 16 of the ocular portion 2 is resistered with the guide pin 65b provided on the connection cover tube 65 of the connector portion 30 for engagement, while the ocular portion 2 and the connection cover tube 65 are pressingly connected to each other. Upon this operation, in the connecting tube 66 of the connector portion 30, the inclined surfaces at the forward ends of the engageable pawls 66c are brought into abutting contact with the side edges of the openings of the bayonet mounts 16a, whereby the connecting tube 66 is firstly rotated in the counterclockwise direction against the biasing forces of the springs 68 as shown in FIGS. 6 and 7, and, when the bayonet engageable pawls 66c go over the openings, the connecting tube 66 is rotated in the clockwise direction by the biasing forces of the springs 68 to thereby be connected in bayonet joint to the bayonet mounts 16a. Furthermore, simultaneously with this bayonet joint, the opening at the forward end of the mouth piece 47 of the gas feed pipe is blocked by the receiving seat 71 of the ocular portion 2.

Connection between the ocular portion 2 and the connector portion 30 by the above-described operation makes it possible to prevent the intrusion of the liquid into a space of connection formed between the end surface portions of the ocular portion 2 and the connector portion 30.

In consequence, even if the endoscope S as a whole is immersed in the washing water as shown in FIG. 2 with this connected state maintained, the endoscope S can be immersed in the liquid without moistening the end face of the ocular portion 2 having the electrodes and the like, which are not desirable to be immersed in the liquid, and the end face of the connector portion 30, which is provided thereon with the electrodes, so that it can be guaranteed that the endoscope S can be safely used after the washing or disinfecting.

Additionally, disconnection of the ocular portion 2 from the connector portion 30 can be carried out by rotating the control ring 63 and further rotating the connecting tube 66 integrally therewith against the biasing forces of the springs 68.

As has been described hereinabove, in the endoscope according to the present invention, the portions not desirable to be immersed in the liquid are hermetically sealingly connected to each other, so that, even after the endoscope as a whole is immersed in the liquid, the endoscope can be immediately used without requiring draining and drying works, etc. Furthermore, the construction of the conventional endoscope can be skilfully utilized to construct the endoscope of this type, so that the endoscope of this type can be obtained without major design change. Further, the endoscope of this type can be wholly immersed in the liquid as described above, and moreover, exclude the dust, etc. which would otherwise adhere to the ocular portion and the like during daily storage. Hence, the functional effects offered by the present invention are outstandingly high.

It should be understood, however, that there is no intention to limit the invention to the specific forms disclosed, but on the contrary, the invention is to cover all modifications, alternate constructions and equivalents falling within the spirit and scope of the invention as expressed in the appended claims.

What is claimed is:

1. An endoscope wherein:
    said endoscope comprises an insertable portion to be inserted into a portion to be observed, a manual control portion secured thereto with the proximal end of said insertable portion, an ocular portion provided on said manual control portion, and a connecting portion secured at one end thereof to said manual control section and provided at the other end thereof with a connector detachably connected to an external apparatus; and
    said connector, when detached from said external apparatus, is water-tightly connectible to said ocular portion.

2. An endoscope as set forth in claim 1, wherein a seal member is interposed between said connectible connector and said ocular portion so as to maintain the water-tightness.

3. An endoscope as set forth in claim 2, wherein said connector can be connected in bayonet joint to said ocular portion.

4. An endoscope as set forth in claim 3, wherein:
    said ocular portion includes an engageable disk for bayonet joint; and
    said connector includes a control ring rotatable and biased in one direction and engageable pawls provided on said control ring and engageable with said engageable disk.

5. An endoscope as set forth in claim 4, wherein:
    said ocular portion includes a visibility adjusting control ring for linearly moving an eye piece and electrode terminals for electrically connecting said ocular portion to a camera; and
    said connector is provided thereon with electrode terminals to be electrically connected to said external apparatus.

* * * * *